(12) United States Patent
Viitanen et al.

(10) Patent No.: US 9,927,412 B2
(45) Date of Patent: Mar. 27, 2018

(54) DUAL GAS SENSOR STRUCTURE AND MEASUREMENT METHOD

(71) Applicant: VAISALA OYJ, Helsinki (FI)

(72) Inventors: Veli-Pekka Viitanen, Helsinki (FI); Kaisa Lehmus, Helsinki (FI); Jukka Leppänen, Luhtajoki (FI)

(73) Assignee: Vaisala Oyj, Helsinki (FI)

( * ) Notice: Subject to any disclaimer, the term of this patent is extended or adjusted under 35 U.S.C. 154(b) by 128 days.

(21) Appl. No.: 14/889,134

(22) PCT Filed: May 27, 2014

(86) PCT No.: PCT/FI2014/050416
§ 371 (c)(1),
(2) Date: Nov. 4, 2015

(87) PCT Pub. No.: WO2014/191619
PCT Pub. Date: Dec. 4, 2014

(65) Prior Publication Data
US 2016/0084811 A1    Mar. 24, 2016

(30) Foreign Application Priority Data
May 30, 2013 (FI) .................................... 20135595

(51) Int. Cl.
*G01N 33/00* (2006.01)
*G01N 27/22* (2006.01)
*G01N 27/12* (2006.01)

(52) U.S. Cl.
CPC ....... *G01N 33/0031* (2013.01); *G01N 27/121* (2013.01); *G01N 27/223* (2013.01); *G01N 33/0024* (2013.01)

(58) Field of Classification Search
CPC .... G01N 27/12; G01N 27/121; G01N 27/223; G01N 27/04; G01N 27/02; G01N 27/00
(Continued)

(56) References Cited

U.S. PATENT DOCUMENTS 4,244,918 A     1/1981   Yasuda et al.
5,362,975 A * 11/1994   von Windheim .... G01N 27/129
                                                     204/410
(Continued)

FOREIGN PATENT DOCUMENTS

DE        4244223 A1    6/1994
DE     19610912 A1    9/1997
(Continued)

OTHER PUBLICATIONS

Supplementary Search Report in EP 14 80 5060, dated Dec. 21, 2016.
(Continued)

*Primary Examiner* — Christine T Mui
(74) *Attorney, Agent, or Firm* — Maschoff Brennan

(57) ABSTRACT

The invention relates to a sensor structure and a method. The sensor structure includes a first sensor having a sensing element sensitive to humidity of the environment. In accordance with the invention the sensor structure also includes s second sensor having a sensing element sensitive to humidity, the second sensor comprising a catalytic permeable layer positioned on the second sensor such that it is between the sensing element of the second sensor and the environment.

24 Claims, 12 Drawing Sheets

(58) Field of Classification Search
USPC .............................................. 422/98, 83, 50
See application file for complete search history.

(56) References Cited

U.S. PATENT DOCUMENTS

| | | | |
|---|---|---|---|
| 6,955,787 B1 * | 10/2005 | Hanson | G01N 29/022 |
| | | | 29/592 |
| 2002/0142478 A1 * | 10/2002 | Wado | G01N 27/124 |
| | | | 436/151 |
| 2004/0026268 A1 | 2/2004 | Maki et al. | |
| 2005/0013726 A1 | 1/2005 | Hill et al. | |

FOREIGN PATENT DOCUMENTS

| | | |
|---|---|---|
| EP | 0334614 A2 | 9/1989 |
| EP | 0665303 A1 | 8/1995 |
| EP | 2009432 A1 | 12/2008 |
| EP | 2418482 A1 | 2/2012 |
| GB | 2011093 A | 7/1979 |
| JP | 2001183326 A | 7/2001 |
| WO | WO2007122287 A1 | 11/2007 |
| WO | WO2008009329 A1 | 1/2008 |

OTHER PUBLICATIONS

International Search Report received in PCT/FI2014/050416, dated Sep. 18, 2014, 7 pgs.

* cited by examiner

DUAL GAS SENSOR STRUCTURE AND MEASUREMENT METHOD

FIELD OF THE INVENTION

The invention relates to a capacitive sensor structure and a method for measuring content of a water soluble chemical in gas in gaseous environment.

Some embodiments of the invention are related to a capacitive sensor structure.

BACKGROUND OF THE INVENTION

In the prior art humidity as such has been measured by capacitive humidity sensors, where the dielectric of the humidity sensor has been sensitive to humidity. By heating also other substances like ammonia have been measured.

Contents of substances like $H_2O_2$ (Hydrogen peroxide), ETO (Ethylene Oxide), and $O_3$ (Ozone) have been measured by electrochemical cells or by IR-optical devices. These devices are very complicated or short-lived and thus also expensive.

Thus, there exists a need for improved sensor and method for measuring content of catalytically degradable substances.

SUMMARY OF THE INVENTION

The method is based on finding that the oxidative gas concentration has influence on observed saturation partial pressure of water vapor. So we can assume that with same partial water pressures we get different RH-values depending on exposure to oxidative gas concentrations. Actually chemical potential is the executive force which causes this phenomenon.

In one embodiment of the invention the sensor structure includes a first sensor having a sensing element sensitive to humidity of the environment, and additionally includes a second sensor having a sensing element sensitive to humidity, the second sensor comprising a catalytic permeable layer positioned on the second sensor such that it is between the sensing element of the second sensor and the environment.

The practical implementation of the invention is based using two humidity sensors: One with catalytically active layer and another without it.

In one embodiment of the invention the two sensors are integrated on the same substrate.

In another implementation the sensor elements are separate units.

In one preferred embodiment one of the sensors is heatable. In an advantageous embodiment the catalytic sensor is heatable.

More specifically, the invention is defined in the independent claims.

The invention provides considerable advantages.

With help of the invention decomposable chemicals like $H_2O_2$ (Hydrogen peroxide), ETO (Ethylene Oxide) or $O_3$ (Ozone) may be detected and the content measured with a simple and inexpensive sensor structure instead of the complicated and expensive prior art solutions like electrochemical cells or by IR-optical devices.

The sensor enables use of novel algorithm based on the determination of the activity of an oxidative gas.

Further, the cost of instrumentation is very low.

According to one embodiment, the sensitivity may be increased by heating the catalytic sensor element.

According to one embodiment, sensor unit cost may be decreased in mass production by integrating the two sensors on the same substrate.

Next, embodiments and advantages of the invention are described in more detail with reference to the attached drawings.

BRIEF DESCRIPTION OF THE DRAWINGS

FIG. 2a shows a sectional view of a sensor structure in accordance with the invention.

FIG. 2b shows a top view of the sensor structure of FIG. 2a.

FIG. 3b shows a top detail of the sensor structure of FIG. 3a.

DETAILED DESCRIPTION OF EMBODIMENTS

Figure 1:
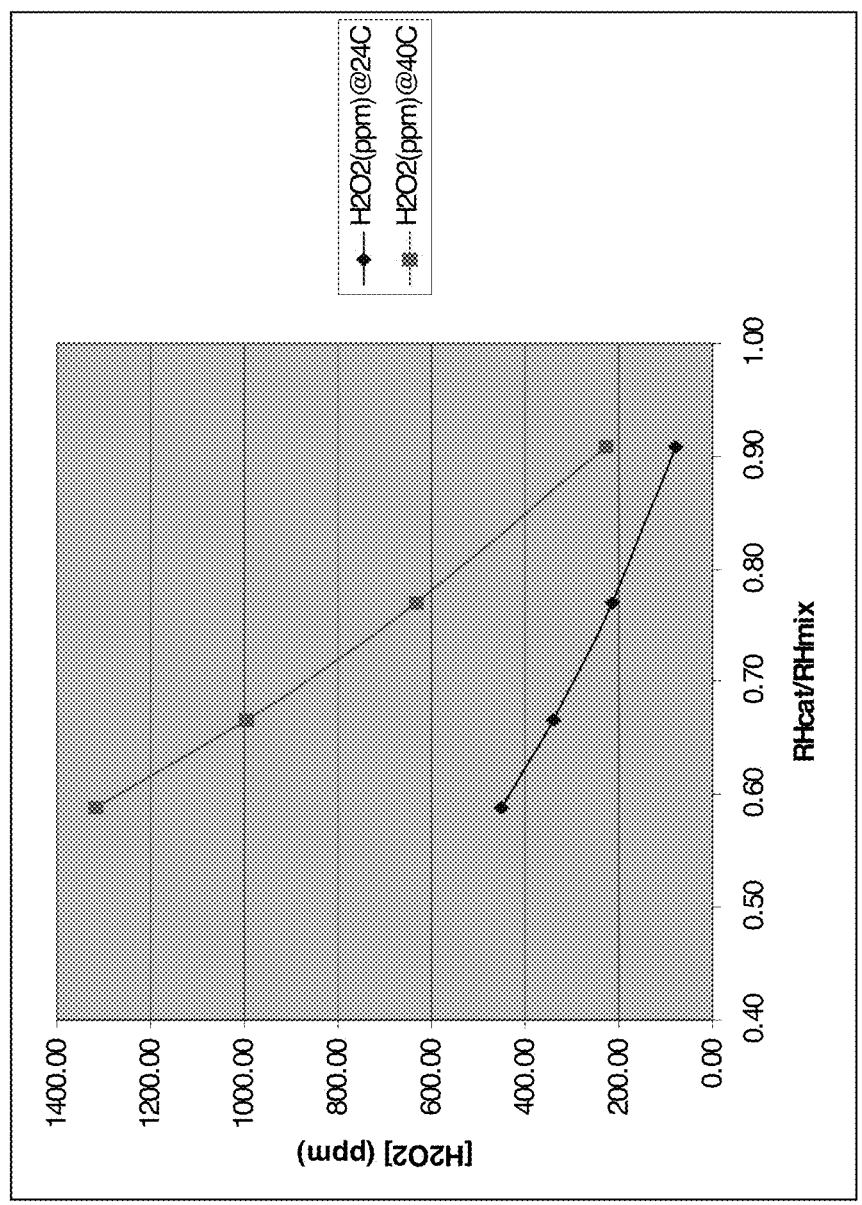
FIG. 1 shows graphically measurement diagrams in accordance with the invention.

The following lists shows the reference numerals used with the terms of the specification:
1 first capacitive humidity sensor
2 second, catalytic capacitive humidity sensor
11 substrate
12 bottom electrode, first electrode
13 polymer dielectric, sensitive dielectric
14 top electrode, second electrode
15 protective polymer
16 porous catalytic metal layer, decomposition layer
17 contact pad
18 heating element
23 general humidity sensitive material
Ox substance to be measured
A catalyzer
B pump
C, D enclosure
E valve, typically magnetic valve

The Principle of the Invention

Basically the capacitive humidity measurement is simply an impedance measurement of a capacitive humidity sensor. The principle is described e.g. in GB-patent 2011093 of the applicant of the present application.

Figures 2A, 2B:
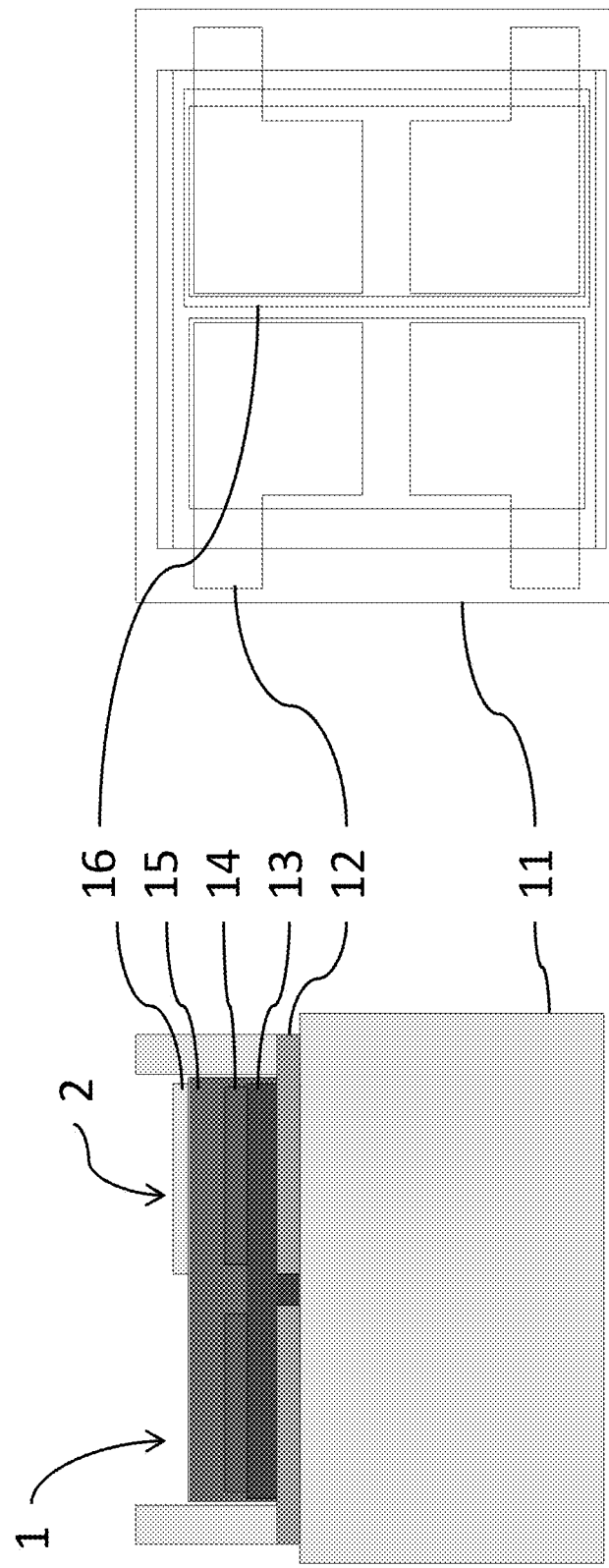

Referring to FIGS. 2a and 2b, based on the basic principle we can formulate equations in case of two sensor measurements, where one is a normal capacitive humidity sensor 1 and the other capacitive humidity sensor 2 with porous catalytic metal layer (decomposition layer) 16:

Definitions

Relative humidity is at all temperatures and pressures defined as the ratio of the water vapour pressure to the saturation water vapour pressure (over water) at the gas temperature:

$$RH = P_w/P_{ws} \cdot 100\% \quad (1)$$

The total pressure does not enter the definition. Above 100° C. the same definition is valid. But as the saturation vapour pressure $P_{ws}$ is greater than 1 013 hPa (normal ambient pressure) the RH cannot reach 100% in an unpressurised system.

Below 0° C. the definition is also valid. Here 100% RH is also impossible because condensation will occur at a lower humidity than 100% (when the vapour is saturated over ice).

In connection with the present invention:

Ox: catalytically degradable substance to be measured for example $H_2O_2$ (Hydrogen peroxide), ETO (Ethylene Oxide), or $O_3$ (Ozone).

RHmix: RH (=Relative Humidity) reading of standard capacitive humidity sensor

RHcat: RH reading of Pt covered capacitive humidity sensor $RHcat = (P_w + P_w(Ox))/P_{ws}$; $P_{ws}$ independent of oxidative gas concentration, $P_w(Ox)$ is vapour pressure of Ox.

And $RHmix = P_w/P_{ws}$mix

As the activity of Ox is a measure for chemical potential and a good approximation for activity is:

$$a(Ox) = [Ox]/[Ox]sat; \text{ and } [Ox]sat = f(T)$$

$$RHcat/RHmix = f(a(Ox)) \text{ and further } a(Ox) = f(RHcat/RHmix)$$

Combining equations it is possible to calculate the hydrogen peroxide concentration if RHcat, RHmix and T are known:

$$[Ox] = f(RHcat/RHmix) * [Ox]sat$$

The measurement is possible to do with discrete sensor elements or integrated elements on one chip. The permeable catalytic layer 16 can be deposited by glancing angle evaporation technics on protective polymer layer 15. Suitable materials are Pt, Rh, silver, $MnO_2$ etc. The oxidative molecules such as $H_2O_2$ (Hydrogen peroxide), ETO (Ethylene Oxide), and $O_3$ (Ozone) decompose over catalytics even without elevated temperature. But it is also possible to enhance decomposition by integrating micro heater e.g. Pt-resistor on the sensor chip.

FIG. 1 shows graphically content of $H_2O_2$ as a function of relation of catalytic humidity measurement (RHcat) and mixed humidity measurement in two different temperatures. The upper curve is performed at 40° C. and the lower at 24° C. Hence, it can be seen that the rise in temperature enhances sensitivity. In other words the graphic is obtained by measuring relative humidity by a normal humidity sensor 1 together with a humidity sensor 2 with a permeable catalytic layer 16.

One embodiment of the sensor is described in FIGS. 2a and 2b, where 2a shows as a sectioned side view the sensor structure, where first sensor 1 is a normal capacitive humidity sensor and the second sensor 2 a catalytic humidity sensor. The structure is formed on a substrate 11, typically a silicon substrate. On the substrate 11 are formed bottom electrodes 12 with contact areas for both sensors 1 and 2. Above the bottom electrodes 12 is formed the sensitive, permeable dielectric layer 13, typically of a suitable polymer. The dielectric properties of the layer 13 are dependent on humidity, in other words $H_2O$ content. Above the dielectric layer 13 are formed top electrodes 14 for both sensors 1 and 2. The water content in the dielectric layer may then be determined by measuring capacitance between the electrodes 12 and 13. A permeable protective layer 15 is formed above the top electrodes 14 and the second sensor is additionally covered with a porous catalytic metal layer, decomposition layer 16 formed e.g. in a process described later.

The metal film above the second sensor 2 is advantageously formed by a method described in the EP-patent 665303 of the applicant of this patent application. In this method the microporous metal film is attained by adjusting an angle alpha between the surface to be metallized and the source evaporating the metal to a value in the range 5-30 degrees. Here the surface to be metalized is the layer 15 or an adhesion layer e.g. of Cr above it. By altering the angle, the porosity and pore size of the metal film can be modified so that a small value of the angle alpha gives an extremely porous layer of large pore size, while a larger value of the angle alpha results in a less permeable layer of smaller pores.

Good adherence is attained by first vacuum evaporating a layer of a slightly self-oxidizing metal (such as Cr, Ni or Ti) to a thickness of 10-300 nm. The plugging of pores through oxidation is prevented by subsequently vacuum evaporating from the same angle a precious metal layer (of Au, Pt or Pd) to a thickness of 10-300 nm. Typically, the total thickness of these layers is in the range 30-400 nm.

Advantageously, the pore size (minimum diameter of the pores) is smaller than 30 nm, whereby a filtering effect against high-molecular-weight molecules is achieved.

Figure 3A:
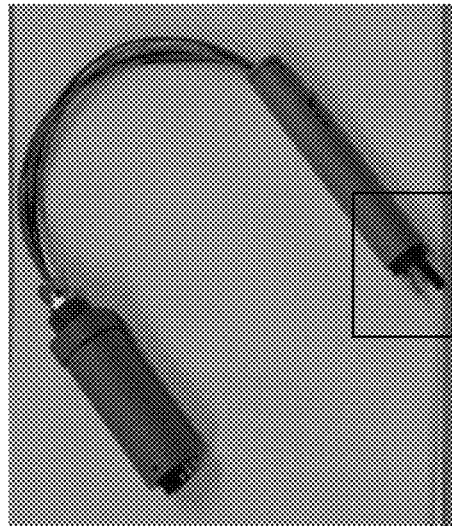
FIG. 3a shows a photograph of one sensor structure in accordance with the invention.
Figure 3B:
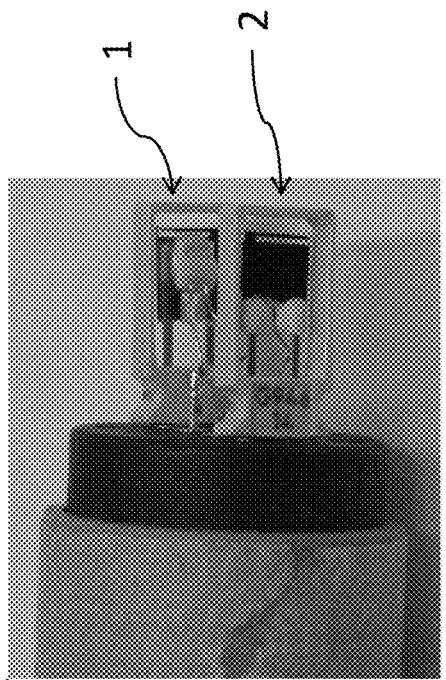

In FIGS. 3a and 3b is presented one embodiment of the sensor structure in accordance with the invention, where the normal capacitive sensor 1 and the catalytic capacitive humidity sensor 2 are independent separate units.

Figure 4:
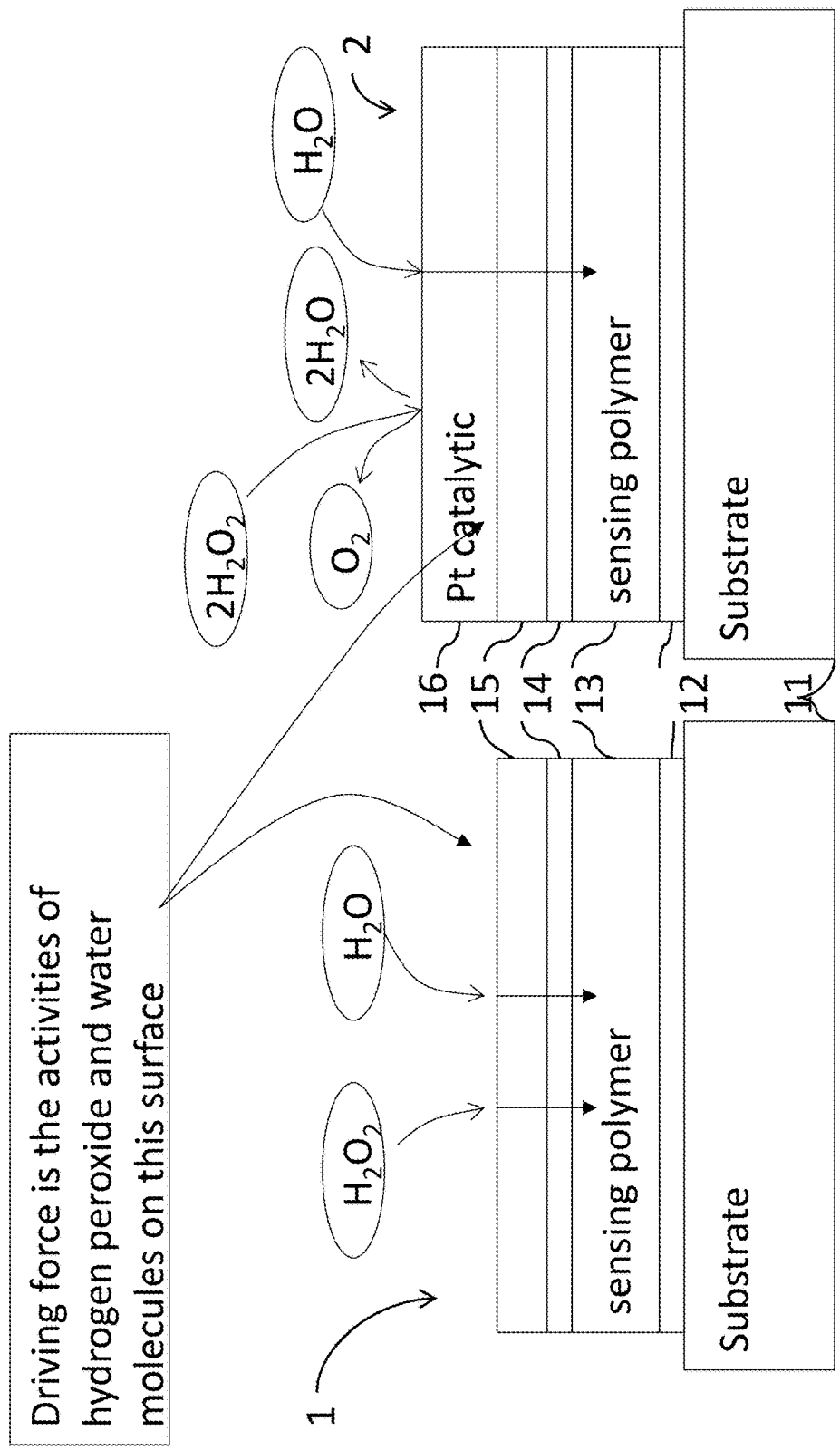
FIG. 4 shows as a schematical side view the principle of the sensor structure of FIGS. 3a and 3b.

This arrangement is presented in more detail in FIG. 4 where also the chemical mechanism of the sensor is more clearly indicated. The catalytic process decomposes $H_2O_2$ into $O_2$ and $H_2O$ and hence changes the reading of sensor 2.

Figure 5:
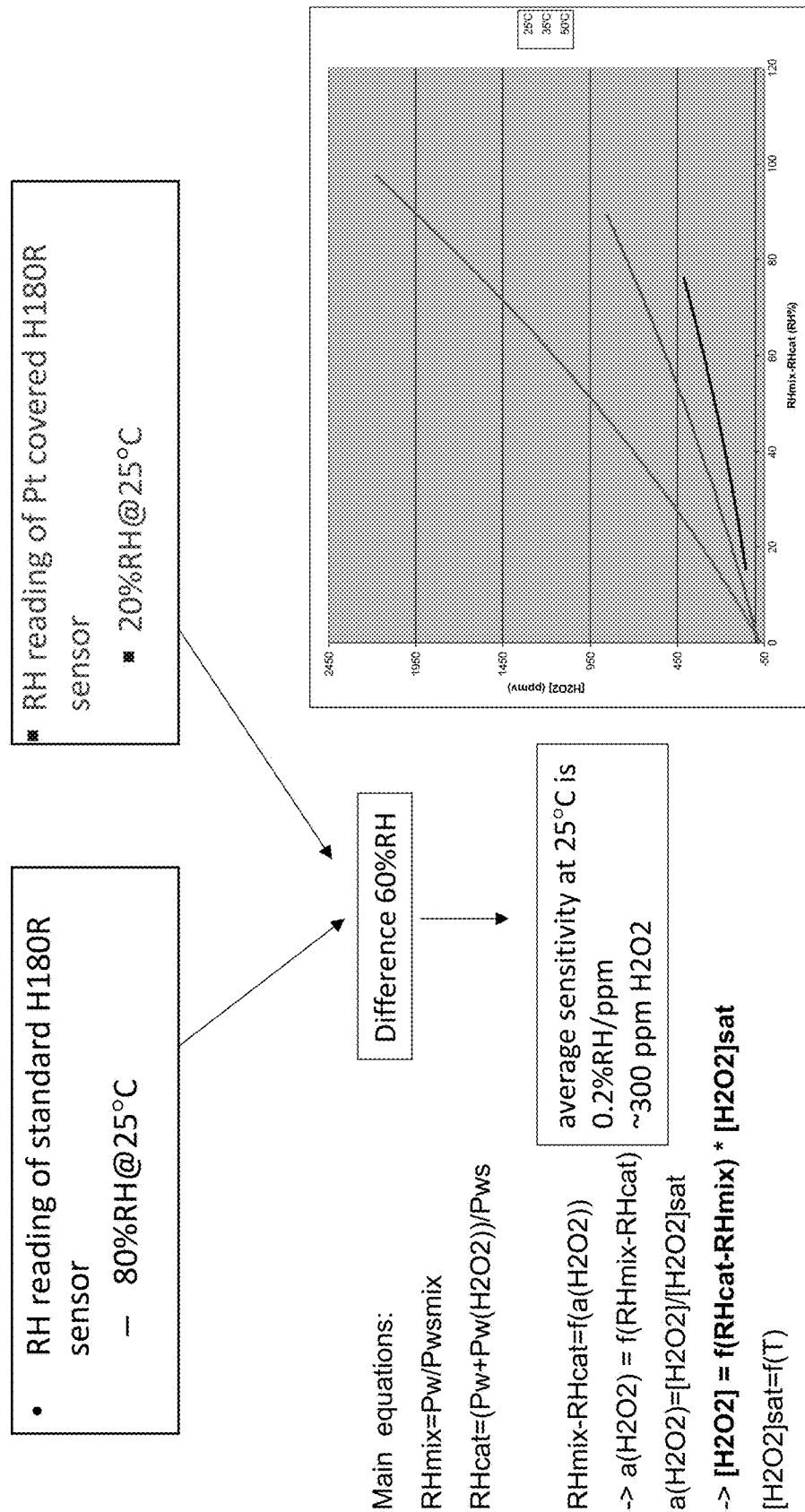
FIG. 5 shows as a block diagram steps of the measurement methods.

FIG. 5 shows the flow chart of the process and indicates how the concentration of substances that can be catalytically decomposed may be indicated.

Figure 6:
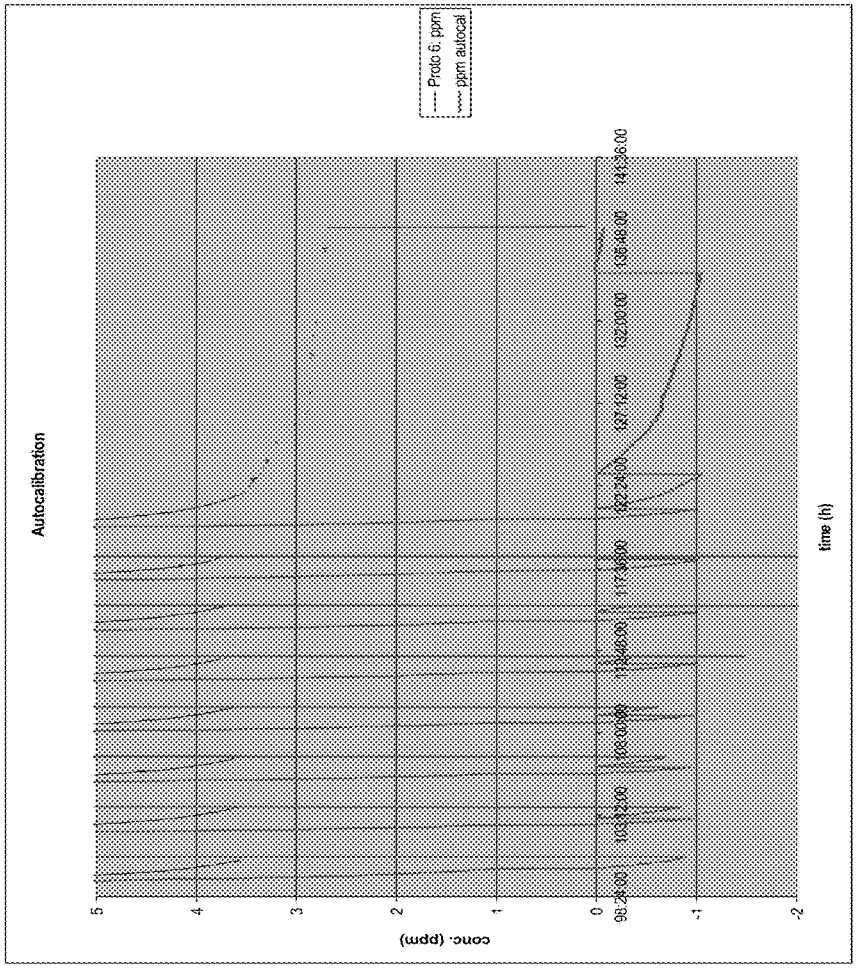
FIG. 6 shows as a graph a possible calibration method in accordance with the invention.

FIG. 6 shows a graph about a method how the sensor in accordance with the invention may be calibrated.

Figure 7:
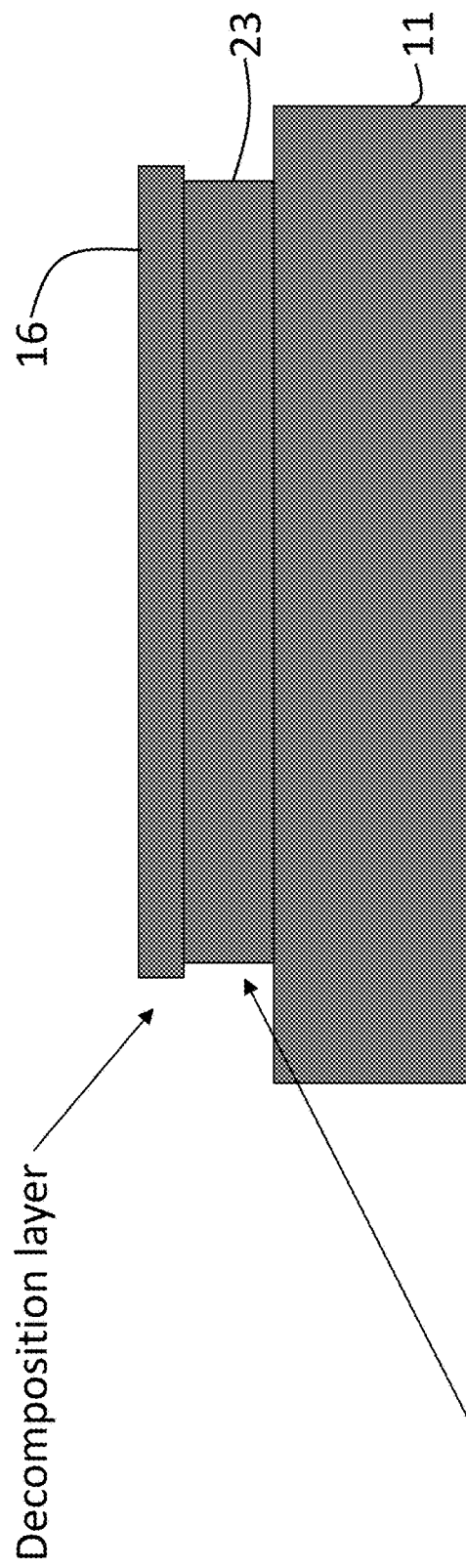
FIG. 7 as a sectional side view a general idea of a sensor structure in accordance with the invention.

In FIG. 7 is presented a general structure for the second sensor in accordance with the invention. In principle the general idea of the invention is to produce a sensor with any kind of humidity sensitive material 26 covered with a decomposition layer 16 and compare the reading of this sensor structure with a reading of corresponding sensor structure without the decomposition layer 26.

Figure 8:
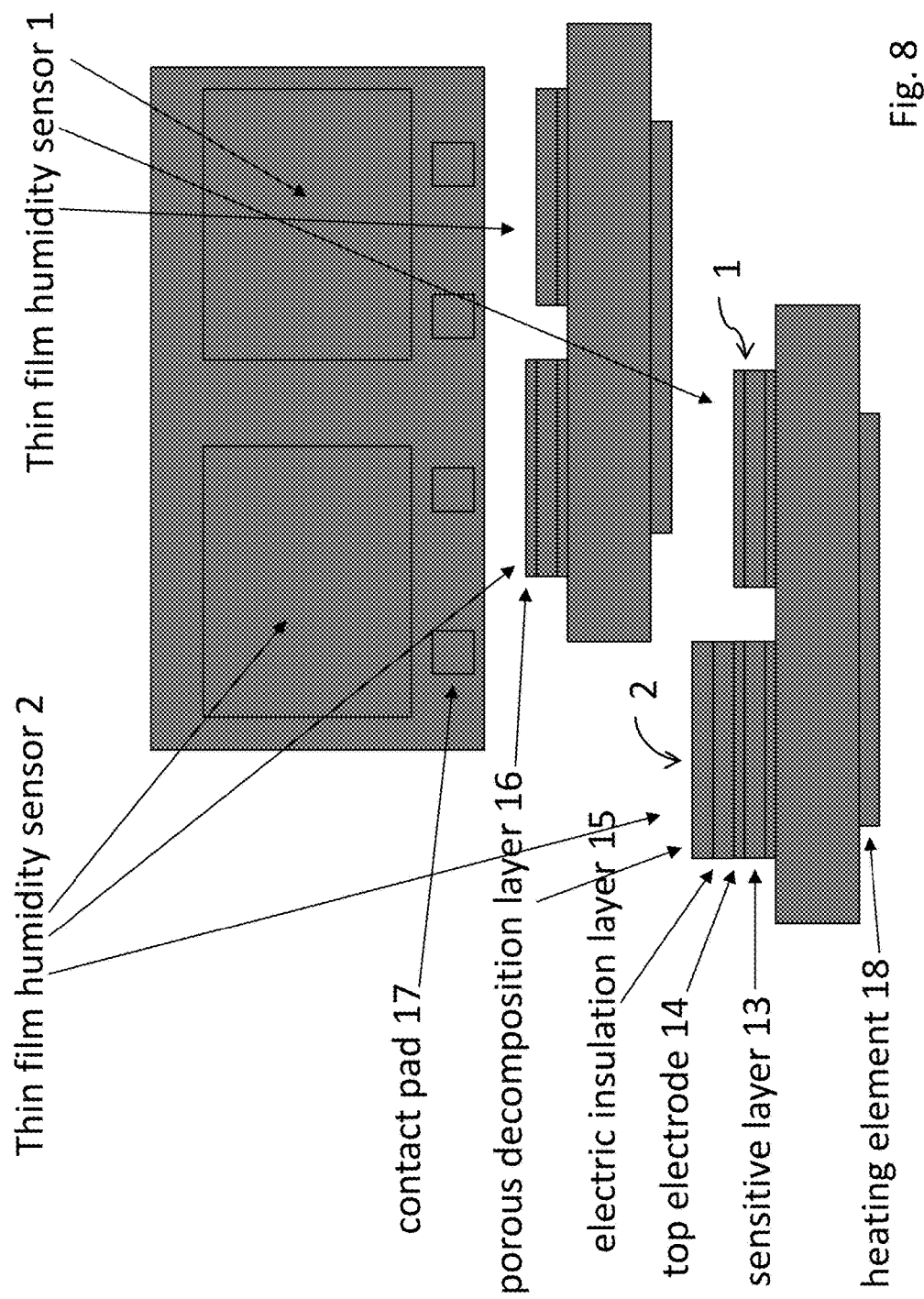
FIG. 8 shows one alternative embodiment of the sensor structure in accordance with the invention.

FIG. 8 presents a sensor structure, where the sensors 1 and 2 are on the same substrate and the structure includes a common heating element 18 beneath the substrate in order to heat both of the elements 1 and 2.

Figure 9:
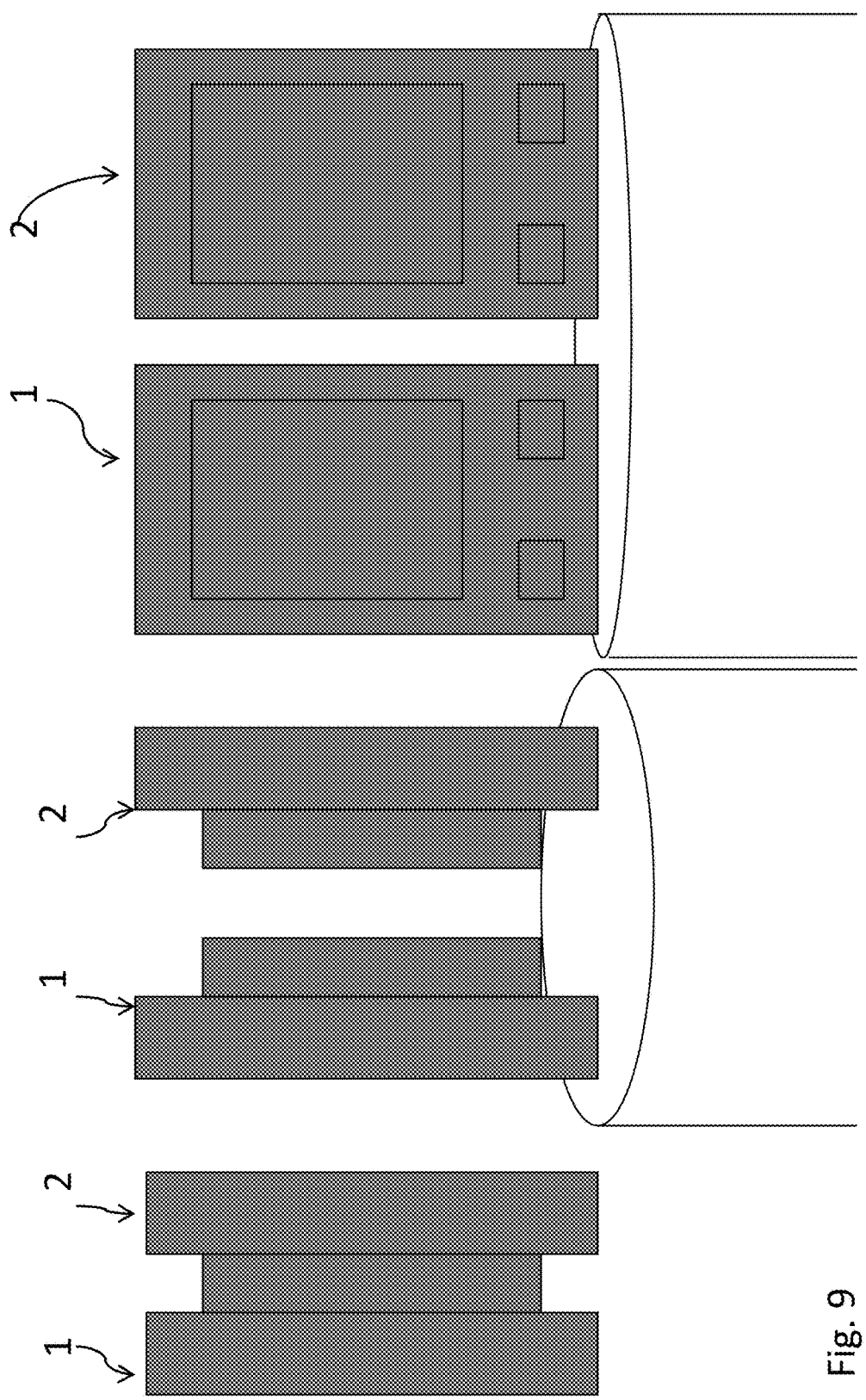
FIG. 9 shows alternative embodiments of the sensor structure in accordance with the invention.

FIG. 9 shows three alternative layouts for sensors 1 and 2.

Figure 10:
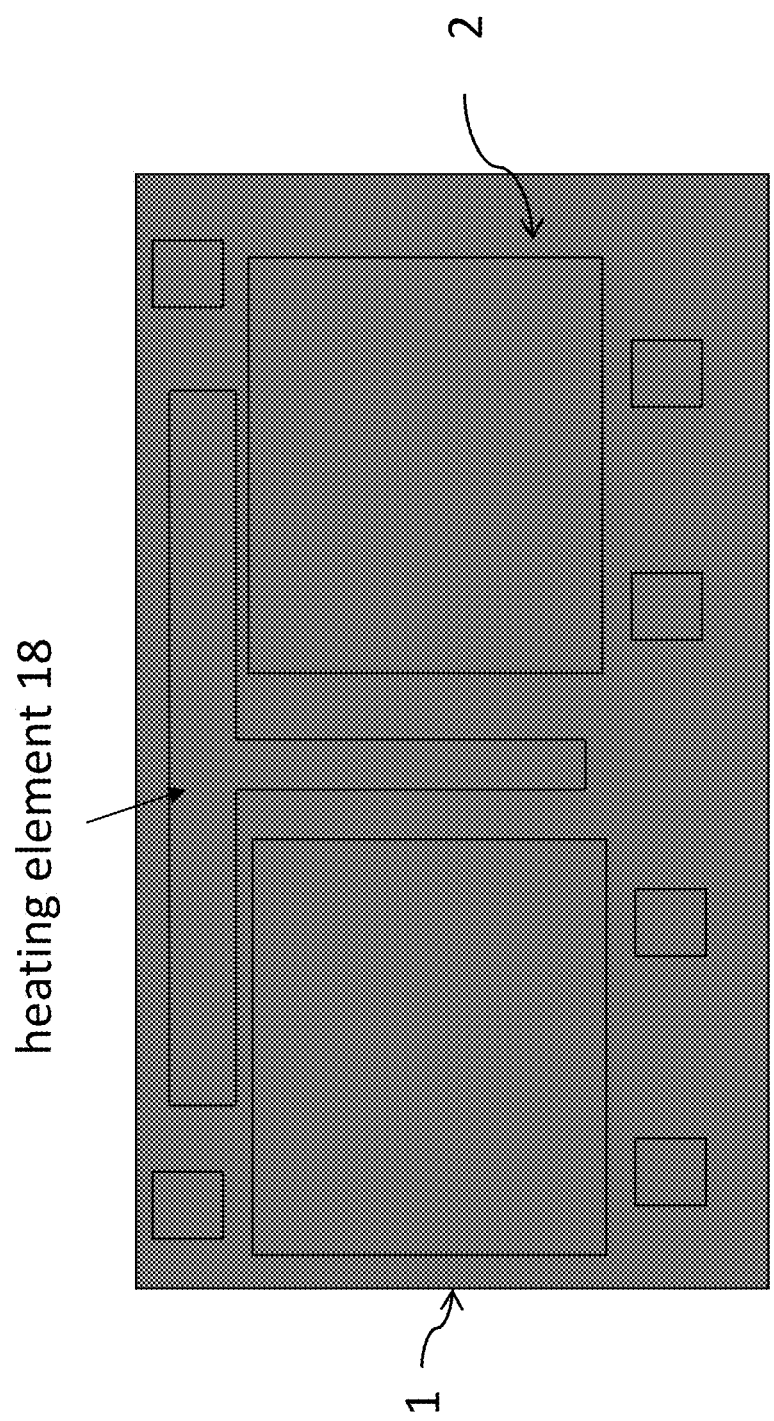
FIG. 10 shows one alternative embodiment of the sensor structure including a heating element in accordance with the invention.

FIG. 10 shows one layout for positioning the heating element in relation to the sensors 1 and 2.

Figure 11:
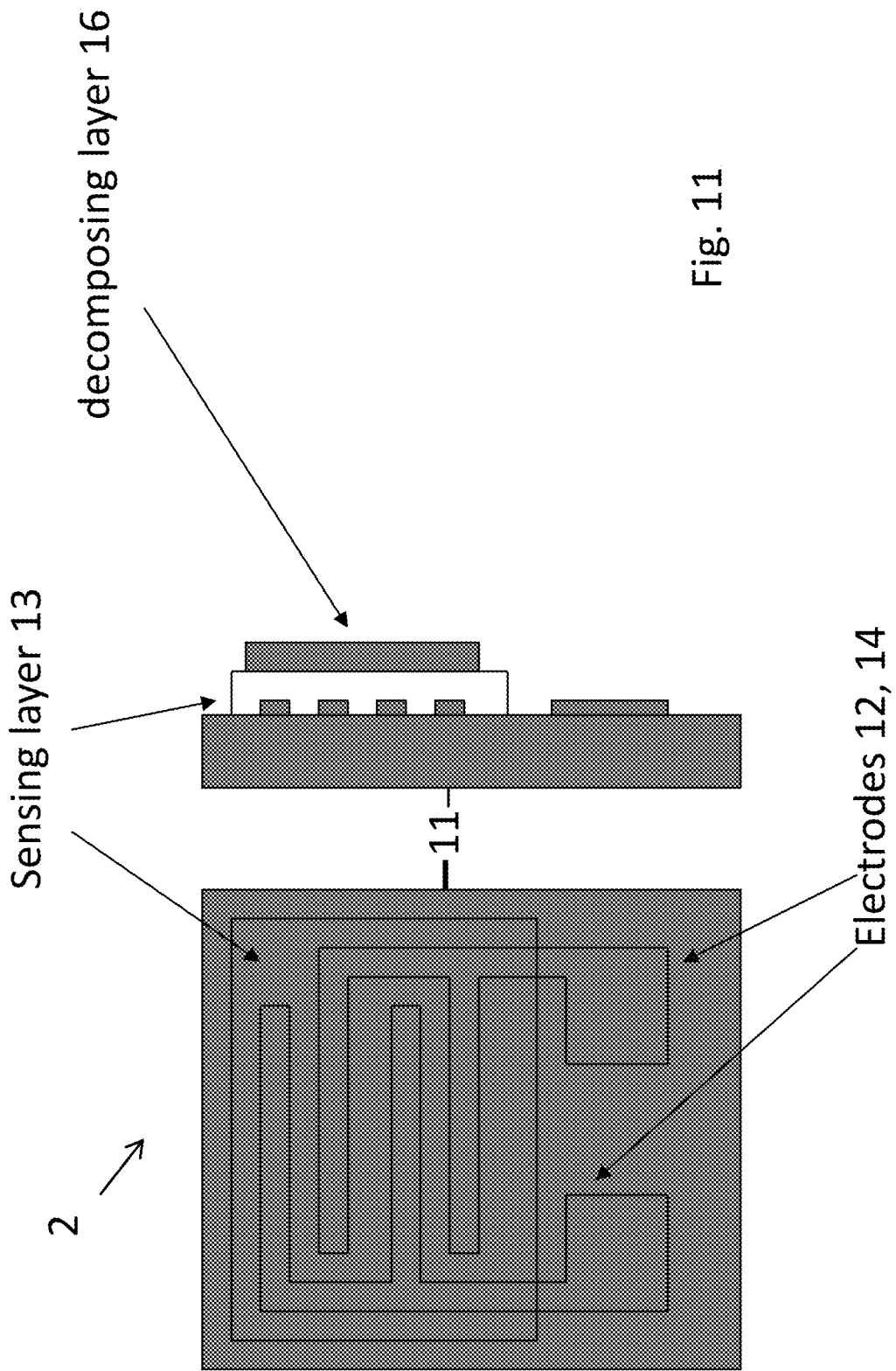
FIG. 11 shows one alternative embodiment of the catalytic sensor structure in accordance with the invention.

FIG. 11 shows one embodiment of the catalytic sensor 2, where the sensing layer is formed above finger-electrodes 12 and 14 and the decomposing layer is positioned above the sensing layer. In the complete sensor structure there is a similar second sensor 1 (not shown) without the decomposing layer 16.

Figures 12A, 12B:
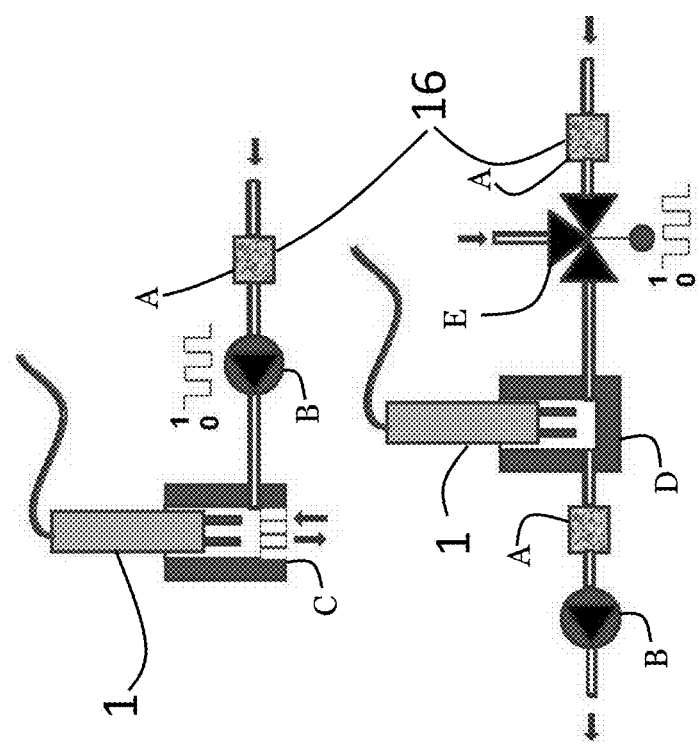
FIGS. 12a and 12b shows alternative measurement systems in accordance with the invention.

In accordance with FIGS. 12a and 12b the measurement system in accordance with one embodiment of the invention can be realized at least in two ways:

According to FIG. 12a using a catalyzer (A) like structure 16 above, a pump (B) and measuring enclosure (C) including a humidity sensor 1 where the enclosure (C) rapidly equilibrates with the ambient gas concentration;

or according to FIG. 12b by using two catalyzers (A) like structure 16 above, a pump (B), a closed measuring enclosure (D) with a humidity sensor 1 and a magnetic valve (E). In this system the enclosure receives in turns gas to the enclosure D either through catalyzer (A) or directly from the target to be measured.

In connection with capacitive humidity sensors the relative humidity may be calculated by a known formula (VIZ) using the temperature information of the ambient air in accordance with the following known formula, when the sensor is heated above the temperature of the ambient air. This principle may be used if heating is used in connection with the present invention.

$$RH_a = RH_s \left[ \frac{eW_s \text{ at } T_s}{eW_s \text{ at } T_a} \right]$$

where
$RH_a$=true relative humidity
$RH_s$=relative humidity of a mixture contiguous with
a humidity sensitive film on a substrate
$eW_s$=the saturation vapor pressure at the substrate
temperature measured by temperature sensor
$eWa$=saturation vapor pressure of the surrounding mixture at temperature $T_a$
$T_s$=substrate temperature measured by temperature sensor
$T_a$=ambient temperature measured by independent sensor Specifications for the Catalytic Sensor 2 in Accordance with FIGS. 3a-3b:

2 capacitance measurements for elements 1 and 2.
2 resistance measurements.
Heating of sensor element 2 triggered by high RH-value.
The humidity sensor 2 with an evaporated catalytic layer (Pt) deposited on protective polymer film may be formed in an advantageous solution with the following parameters:

Pt-layer 16 is evaporated on 14° angle.
Thickness of Pt layer 16 is typically 1000 nm.
Adhesion layer Cr (thickness about 50 nm) is formed between polymer 15 and Pt-layer 16.
Protection layer is formed on CrNiAu-lead (LIMA: SiAlOx).

As a conclusion the measurement is based on measurement of two RH-sensors 1 and 2. One with a catalytic protection layer 2 is used to measure partial water pressure (RHcat) and the other 1 without the catalytic layer is used to indicate mixture of hydrogen peroxide and water (RHmix).

The catalytic sensor 2 comprises e.g. a Pt layer 16 as catalytic decomposer purpose to prevent $H_2O_2$ penetration in sensing polymer.

Difference between readings of the sensors RHmix (sensor 1) and RHcat (sensor 2) indicates the vapor concentration of $H_2O_2$.

In the following equations when a calibration option with sensor heating is used in accordance with FIG. 6:

$RH\text{mix}=Pw/Pw\text{smix}$ $RH\text{cat}=(Pw+Pw(H_2O_2))/Pws$

<1 ppm $H_2O_2$ then $RH\text{mix}=RH\text{cat}$ or

<−1 ppm $H_2O_2$ then $RH\text{mix}=RH\text{cat}$

This is executed by changing Cdry of RHmix sensor.
Method works if drift in one sterilization cycle is less than 1 ppm (0.4% RH in 25° C.)

Alternative Solutions of the Invention:
Suitable materials for the porous decomposition layer 16 are listed in the following:

Pt, Rh, Ag, Mn or other transition metal and their compounds.

Objects to be measured are listed in the following:
hydrogen peroxide, ozone, peracetic acid or other catalytically degradable substance.

As humidity sensors may be used any humidity sensor structures that can be measured electrically.

The measurement may be based e.g. on:
impedance, like capacitive or resistive or inductive sensors
resonators like BAW, SAW etc.
semiconductors Essential for the invention is an element, typically a layer 13 sensitive to humidity, especially to relative humidity. The sensitivity may be based on change of permittivity (capacitive measurement), conductivity (measurement of resistivity) or mass (resonators). Materials sensitive for these parameters are polymers, ceramics and composites.

The material 13 sensitive to the relative humidity may be positioned on the sensor or sensor field or inside the sensor structure, typically between sensor layers. Also cylindrical structures are possible.

The catalytic layer (decomposition layer) 16 may also act as a surface electrode for the measurement.

In connection with the invention the catalytic permeable layer 16 encloses the sensing element 13 at least essentially. This means in practice that the catalytic permeable layer 16 has to cover the sensing element 13 so well that the decomposition happens to the substance Ox to be measured in such a way that content of Ox may be calculated. Typically the coverage of the sensing element 13 by the layer 16 is around 70-100%, most preferably around 90-98%.

In one embodiment of the invention only one sensor may be used but the measurement is made such that the sensor gets sequentially measurement gas in a first phase directly from the space to be measured and in the second phase through a catalytic permeable layer 16 and these results from these two phases will be compared like the results of the two sensors 1 and 2 in the other embodiments of the invention. In this embodiment the permeable catalytic layer 16 may function also as a particle filter for the sensor.

In accordance with the invention the catalytic permeable layer 16 is only one embodiment of the invention. The catalytic reaction needed for reference measurement may be performed in many ways, for example by a catalytic matrix structure, catalytic particle filter, catalytic particle cloud in a fluidized filter structure etc.

The reference measurement by one sensor on the other hand may be performed in a sequentially with alternating flows through the sensor either directly from the object to be measured or through or in contact with a material reacting catalytically with the gas to be measured. Then the two measurements will be compared repeatedly with each other in accordance with the two sensor measurement described above.

In one preferred embodiment of the invention with two sensors at least one reference measurement is made with such a gas that does not include the gas to be measured (Ox) in order to compensate any difference between the two sensor readings. By this procedure drifting or the sensors may be eliminated.

What is claimed is:

1. A sensor structure comprising:
   a first sensor positioned in an environment and having a sensing element sensitive to humidity of the environment; and
   a second sensor having a sensing element sensitive to humidity, the second sensor comprising a catalytic permeable layer positioned on the second sensor such that it is between the sensing element of the second sensor and the same environment.

2. The sensor structure in accordance with claim 1, further comprising a capacitive humidity sensor, having:
   a first electrode;
   a second electrode; and
   a sensitive dielectric positioned between the electrodes, wherein:
      the sensor structure includes additionally another capacitive humidity sensor, comprising a catalytic permeable layer positioned on the second sensor such that it is between the sensing element of the second sensor and the environment.

3. The sensor structure in accordance with claim 2, wherein the catalytic permeable layer is formed above a protective polymer layer formed above one of the electrodes.

4. The sensor structure in accordance with claim 1, wherein the catalytic permeable layer is formed above an adhesion layer formed over a protective polymer layer.

5. The sensor structure in accordance with claim 4, wherein the adhesion layer is of Cr.

6. The sensor structure in accordance with claim 1, wherein the first sensor and the second sensor are formed on a same substrate.

7. The sensor structure in accordance with claim 1, wherein the sensors are mechanically not connected.

8. The sensor structure in accordance with claim 1, further comprising a heating element.

9. The sensor structure in accordance with claim 1, wherein a material for the catalytic permeable layer is selected from Pt, Rh, Ag, Mn or other transition metal and their compounds.

10. The sensor structure in accordance with claim 1, wherein the catalytic permeable layer is formed by vacuum evaporating where source evaporating a metal is adjusted into an angle relative to the sensor structure to a value in the range 5-30 degrees.

11. The sensor structure in accordance with claim 1, wherein the sensors are resistive sensors.

12. The sensor structure in accordance with claim 1, wherein the first sensor and the second sensor are resonators.

13. The sensor structure in accordance with claim 1, wherein the catalytic permeable layer is also an electrode.

14. The sensor structure in accordance with claim 1, wherein the sensor structure is configured to make a humidity measurement based on a capacitive measurement.

15. The sensor structure in accordance with claim 1, wherein the sensor structure is configured to make a humidity measurement based on a resistive measurement.

16. The sensor structure in accordance with claim 1, wherein the sensor structure is configured to make a humidity measurement based on a resonance measurement.

17. The sensor structure in accordance with claim 1, wherein a ratio between a first measurement of the first sensor and a second measurement of the second sensor is formed in order to define content of a catalytically degradable substance to be measured.

18. The sensor structure in accordance with claim 1, wherein a difference between a first measurement of the first sensor and a second measurement of the second sensor is formed in order to define content of a catalytically degradable substance to be measured.

19. The sensor structure in accordance with claim 1, wherein at least one of the sensors is heated during a measurement in order to enhance sensitivity.

20. The sensor structure in accordance with claim 1 wherein the first sensor and the second sensor are SAW resonators.

21. The sensor structure in accordance with claim 1 wherein the first sensor and the second sensor are BAW resonators.

22. The sensor structure in accordance with claim 1 wherein the first sensor and the second sensor share a single dielectric.

23. The sensor structure in accordance with claim 1 wherein the first sensor and the second sensor share a common protective polymer layer.

24. The sensor structure in accordance with claim 1, wherein:
   the first sensor further comprises:
      a first electrode; and
      a second electrode
   the second sensor further comprises:
      a third electrode; and
      a fourth electrode; and
   the sensor structure further comprises:
      a common substrate positioned beneath the first and third electrodes;
      a common dielectric layer positioned between the first and second electrodes and between the third and fourth electrodes; and
      a common protective polymer layer positioned above the second and fourth electrodes.

* * * * *